Figure 3:
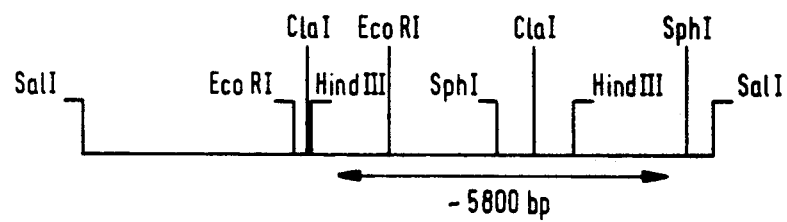

United States Patent [19]
Ebeling et al.

[11] Patent Number: 5,126,256
[45] Date of Patent: Jun. 30, 1992

[54] **PROCESS FOR THE PREPARATION OF GLUCOSE DEHYDROGENASE FROM *BACILLUS MEGATERIUM***

[75] Inventors: Wolfgang Ebeling, Bickenbach; Hans J. Heilmann, Griesheim; Friedhelm Meinhardt, Erckenschwick, all of Fed. Rep. of Germany

[73] Assignee: Merck Patent Gesellschaft mit Beschrankter Haftung, Darmstadt, Fed. Rep. of Germany

[21] Appl. No.: 179,359

[22] Filed: Apr. 8, 1988

[30] Foreign Application Priority Data

Apr. 8, 1987 [DE] Fed. Rep. of Germany ....... 3711881

[51] Int. Cl.$^5$ .................. C12N 9/04; C12N 15/53; C12N 1; C12N 21; C12N 5/10
[52] U.S. Cl. .................. 435/190; 435/240.1; 435/252.3; 435/252.31; 435/252.33; 435/320.1; 435/172.3; 536/27

[58] Field of Search .................. 435/69.1, 190, 172.3, 435/252.3, 252.33, 320; 536/27; 935/1, 29, 73

[56] References Cited

U.S. PATENT DOCUMENTS 4,582,800 4/1986 Crowl .................................. 435/70

OTHER PUBLICATIONS

Lampel, et al. *J. Bacti*, 166(1):238-243, 1986.
Jany, et al *FEBS Lett*, 165(1):6-10, 1984.
Suggs, et al *PNAS USA*, 78(11):6613-6617, 1981.

*Primary Examiner*—Richard A. Schwartz
*Assistant Examiner*—Richard M. Lebovitz
*Attorney, Agent, or Firm*—Millen, White & Zelano

[57] ABSTRACT

A process for the preparation of glucose dehydrogenase from *Bacillus megaterium*. This invention relates to the preparation of a genetically engineered polypeptide with the biological activity of the enzyme glucose dehydrogenase, and a new DNA sequence, recombinant DNA vector, and transformed microorganism therefor.

17 Claims, 8 Drawing Sheets

FIG. 1

ATG-TAT-ACA-GAT-TTA-AAA-GAT-AAA-GTA-GTT-GTA-ATT-
ACA-GGT-GGA-TCA-ACA-GGT-TTA-GGA-CGC-GGA-ATG-GCT-
GTT-CGT-TTC-GGT-CAA-GAA-GAA-GCA-AAA-GTT-GTT-ATT-
AAC-TAT-TAC-AAC-AAT-GAA-GAA-GAA-GCT-CTA-GAT-GCG-
AAA-AAA-GAA-GTA-GAA-GAA-GCA-GGC-GGA-CAA-GCA-ATC-
ATC-GTT-CAA-GGC-GAT-GTA-ACA-AAA-GAA-GAA-GAC-GTT-
GTA-AAT-CTT-GTT-CAA-ACA-GCT-ATT-AAA-GAA-TTT-GGT-
ACA-TTA-GAC-GTA-ATG-ATT-AAC-AAC-GCT-GGT-GTT-GAA-
AAC-CCA-GTT-CCT-TCT-CAT-GAG-CTA-TCT-CTA-GAT-AAC-
TGG-AAC-AAA-GTT-ATT-GAT-ACA-AAC-TTA-ACA-GGT-GCA-
TTC-TTA-GGA-AGC-CGT-GAA-GCA-ATT-AAA-TAC-TTC-GTT-
GAA-AAC-GAC-ATT-AAA-GGA-AAT-GTT-ATC-AAC-ATG-TCT-
AGC-GTT-CAC-GAA-ATG-ATT-CCT-TGG-CCA-TTA-TTT-GTT-
CAC-TAC-GCA-GCA-AGT-AAA-GGC-GGT-ATG-AAA-CTA-ATG-
ACG-GAA-ACA-TTG-GCT-CTT-GAA-TAT-GCG-CCA-AAA-GGT-
ATT-CGC-GTA-AAT-AAT-ATT-GGA-CCA-GGT-GCG-ATG-AAC-
ACA-CCA-ATT-AAC-GCA-GAG-AAA-TTT-GCA-GAT-CCA-GAA-
CAA-CGT-GCA-GAC-GTA-GAA-AGC-ATG-ATT-CCA-ATG-GGT-
TAC-ATC-GGT-AAA-CCA-GAA-GAA-GTA-GCA-GCA-GTT-GCA-
GCA-TTC-TTA-GCT-TCA-TCA-CAA-GCA-AGC-TAT-GTA-ACA-
GGT-ATT-ACA-TTA-TTT-GCA-GAT-GGC-GGT-ATG-ACG-AAA-
TAC-CCT-TCT-TTC-CAA-GCA-GGA-AGA-GGC-TAA-TAG

FIG.2

Met-Tyr-Thr-Asp-Leu-Lys-Asp-Lys-Val-Val-Val-Ile-
Thr-Gly-Gly-Ser-Thr-Gly-Leu-Gly-Arg-Ala-Met-Ala-
Val-Arg-Phe-Gly-Gln-Glu-Glu-Ala-Lys-Val-Val-Ile-
Asn-Tyr-Tyr-Asn-Asn-Glu-Glu-Glu-Ala-Leu-Asp-Ala-
Lys-Lys-Glu-Val-Glu-Glu-Ala-Gly-Gly-Gln-Ala-Ile-
Ile-Val-Gln-Gly-Asp-Val-Thr-Lys-Glu-Glu-Asp-Val-
Val-Asn-Leu-Val-Gln-Thr-Ala-Ile-Lys-Glu-Phe-Gly-
Thr-Leu-Asp-Val-Met-Ile-Asn-Asn-Ala-Gly-Val-Glu-
Asn-Pro-Val-Pro-Ser-His-Glu-Leu-Ser-Leu-Asp-Asn-
Trp-Asn-Lys-Val-Ile-Asp-Thr-Asn-Leu-Thr-Gly-Ala-
Phe-Leu-Gly-Ser-Arg-Glu-Ala-Ile-Lys-Tyr-Phe-Val-
Glu-Asn-Asp-Ile-Lys-Gly-Asn-Val-Ile-Asn-Met-Ser-
Ser-Val-His-Glu-Met-Ile-Pro-Trp-Pro-Leu-Phe-Val-
His-Tyr-Ala-Ala-Ser-Lys-Gly-Gly-Met-Lys-Leu-Met-
Thr-Glu-Thr-Leu-Ala-Leu-Gly-Tyr-Ala-Pro-Lys-Gly-
Ile-Arg-Val-Asn-Asn-Ile-Gly-Pro-Gly-Ala-Met-Asn-
Thr-Pro-Ile-Asn-Ala-Glu-Lys-Phe-Ala-Asp-Pro-Glu-
Gln-Arg-Ala-Asp-Val-Glu-Ser-Met-Ile-Pro-Met-Gly-
Tyr-Ile-Gly-Lys-Pro-Glu-Glu-Val-Ala-Ala-Val-Ala-
Ala-Phe-Leu-Ala-Ser-Ser-Gln-Ala-Ser-Tyr-Val-Thr-
Gly-Ile-Thr-Leu-Phe-Ala-Asp-Gly-Gly-Met-Thr-Lys-
Tyr-Pro-Ser-Phe-Gln-Ala-Gly-Arg-Gly

FIG. 7 a    Met-Tyr-Thr-Asp-Leu-Lys-Asp-Lys-Val-Val-Val-Ile-Thr-Gly-Glyb    Met-Tyr-Lys-Asp-Leu-Glu-Gly-Lys-Val-Val-Val-Ile-Thr-Gly-Sera    Ser-Thr-Gly-Leu-Gly-Arg-Ala-Met-Ala-Val-Arg-Phe-Gly-Gln-Glub    Ser-Thr-Gly-Leu-Gly-Lys-Ser-Met-Ala-Ile-Arg-Phe-Ala-Thr-Glua    Glu-Ala-Lys-Val-Val-Ile-Asn-Tyr-Tyr-Asn-Asn-Glu-Glu-Glu-Alab    Lys-ala-Lys-Val-Val-Val-Asn-Tyr-Arg-Ser-Lys-Glu-Asp-Glu-Ala-

PROCESS FOR THE PREPARATION OF GLUCOSE DEHYDROGENASE FROM *BACILLUS MEGATERIUM*

CROSS-REFERENCE TO RELATED APPLICATION

This application is related to U.S. Ser. No. 07/179,429, filed on even date, now abandoned, whose entire disclosure is incorporated by reference herein.

SUMMARY OF THE INVENTION

The invention relates to a genetic engineering process for the preparation of glucose dehydrogenase. This comprises the enzyme glucose dehydrogenase being isolated from a cultivated microbial host organism after the host has previously been transformed with appropriate recombinant DNA. The recombinant DNA contains a sequence which originates from a genome of Bacillus megaterium and codes for a polypeptide having the biological activity of glucose dehydrogenase.

The invention also relates to the provision of a DNA sequence which codes for a polypeptide having the biological activity of the enzyme glucose dehydrogenase.

Moreover, the invention relates to cloning and expression vectors for use for the preparation of a polypeptide having the biological activity of the enzyme glucose dehydrogenase, and to host organisms transformed with such vectors, for example bacteria, yeasts, other fungi, animal or human cells. Finally, the invention relates to the use, for the determination of glucose, of the corresponding polypeptides whose expression has been brought about. The term "polypeptide having the biological activity of the enzyme glucose dehydrogenase" includes, for example, a polypeptide or protein whose amino acid sequence corresponds to the natural glucose dehydrogenase from *Bacillus megaterium* strains, is similar to this sequence or embraces an enzymatically active fragment. Analogous statements apply also to those polypeptides according to the invention in which the natural sequence represents only a fragment.

NAD/NADP-dependent glucose dehydrogenase (E.C. 1.1.1.47), called glucose DH hereinafter, catalyzes the conversion of $\beta$-glucose into gluconolactone, during which reaction the cofactor NAD is reduced to $NADH_2$. The enzyme is distinguished by high substrate specificity with regard to $\beta$-D-glucose. Epimeric sugars are not converted. The main use of the enzyme is in medical diagnostic techniques. NAD-dependent glucose DH occurs in a range of Bacillus species. The production of this enzyme is subject to developmental physiological control, that is to say it is synthesized only during a short phase of sporulation. In addition, glucose DH is in most cases associated with $NADH_2$ oxidases which seriously interfere with the determination of glucose by the above-mentioned glucose DH method and, moreover, can be removed only with difficulty. All this has the consequence that the yields of enzyme obtained with customary classical methods and using wild Bacillus strains are very modest (0.01 to a maximum of 0.1 units/ml of culture). It is possible by use of known strain-improvement methods to select strains in which glucose DH production is still detectable irrespective of the sporulation phase (mean enzyme activities 1 to 10 units/ml of culture), but such "decoupled" strains may readily revert, that is to say return to the original sporulation behavior, so that the continuous, and frequently protracted, effort must be applied to keep sporulation and glucose DH production separate from one another. Although there has recently (Vasantha et al., 1983, Proc. Natl. Acad. Science, U.S.A., Vol. 80, 785-789) been successful isolation of a gene encoding glucose DH, including its promoter, from *Bacillus subtilis*, and sporulation-independent expression thereof in *E. coli*, surprisingly this enzyme proved to be rather unstable, (loss of activity during the glucose DH-test) in contrast to the commercially available glucose DH (Ramaley, Vasantha 1983, J. Biol. Chem., Vol. 258, 20, 12558-12565). However, high enzyme stability is particularly necessary to be able to carry out a rapid and reproducible glucose determination assay.

Thus, it is an object of this invention to provide a genetic engineering method which permits the industrial preparation of a stable glucose dehydrogenase in large amounts and of improved quality. This object is achieved as indicated hereinafter.

Upon further study of the specification and appended claims, further objects and advantages of this invention will become apparent to those skilled in the art.

It has been found, surprisingly, that by screening a genomic library of *Bacillus megaterium* in a phage vector, preferably $\lambda$-EMBL-3, successive reduction in size of the DNA region carrying the structural gener, and transformation each time of a host organism, in particular *E. coli*, it is possible to obtain at least two different structural genes separately, which finally results in the expression of at least two different glucose DH isoenzymes with improvement of quality and quantity.

Whereas one identified DNA region which encodes glucose DH and is 2100 base pairs (bp) in size entirely corresponds in the DNA and amino acid sequence to the known sequence of commercially available glucose DH (Jany et al., 1984, FEBS Lett. 165; 6-10), the other DNA fragment, which is 1100 bp in size, has the new sequence depicted in FIG. 1. The new amino acid sequence derived therefrom and confirmed by protein sequencing of the purified enzyme is reproduced in FIG. 2. The difference from the known sequence amounts to almost 20%. The differences in the first 45 amino acids are depicted in FIG. 7. If these various DNA fragments are incorporated into plasmid vectors suitable for this purpose (for example pJH111 and pJH211), and appropriate host organisms are transformed, preferably *E. coli* cells, then, merely by use of a promoter intrinsic to Bacilli and active in *E. coli*, the glucose DH enzyme activities obtained in both cases are from 0.05 to 0.5 units/ml of culture, preferably 0.09 to 0.2 units/ml of culture. This already exceeds, by a factor of at least 5, the figures obtainable by classical methods for wild Bacillus strains. Incorporation of the known controllable $\lambda$ $P_L$ promoter upstream of the particular structural gene leads to surprisingly high measured enzyme activities: 30-65 units/ml of culture, preferably 40-50 units/ml of culture, when the new polypeptide shown in FIG. 2 is used with *E. coli* N100/pRK248/pJH115, and 20-40 units/ml of culture, preferably 25-35 units/ml of culture, when the polypeptide of the known sequence is used with *E. coli* N100/pRK248/pJH215. These figures are about 500 times higher than the glucose DH yield with wild Bacillus strains, and about 5-10 times higher than with the sporulation-decoupled Bacillus strains whose development and maintenance is elaborate. A typical growth and expression curve is reproduced in FIG. 8, for *E. coli* N100/pRK248/pJH115 by way of example.

However, besides the considerable increase in activity, the process according to the invention also has further advantages. Thus, all the sporulation problems in *E. coli* are eliminated. A host strain prepared by the new process can thus be used considerably more straight-forwardly and economically. Furthermore, the crude extracts of the *E. coli* host cells producing glucose DH in the new process exhibit no pigmentation whatever (clear colorless liquid), whereas the crude extracts prepared in the conventional manner are very dark green to black in color and require further purification. Furthermore, the content of interfering $NADH_2$ oxidases in a crude extract prepared by the new genetic engineering process is negligible. The purity in terms of foreign protein content is evident from FIG. 9. The host cells containing the recombinant DNA also exhibit astonishingly great plasmid stability; moreover, the relevant expression products have good enzyme stability, which must be guaranteed for diagnostic purposes. This is evidently another distinct advantage compared with the known *Bacillus subtilis/E. coli* system.

Thus the process according to the invention exhibits crucial advantages over the state of the art.

Hence the invention relates to a process for the preparation of glucose DH by cultivation, in a nutrient medium, of a microbial host organism which has been transformed with recombinant DNA, and isolation of the various polypeptides whose expression has been brought about, which is characterized by use of a host organism which contains a DNA region which has been isolated from the genome of *Bacillus megaterium* and which codes for one or more polypeptides having the biological activity of the enzyme glucose DH.

The invention likewise relates to the DNA sequence shown in FIG. 1, which codes for a polypeptide having the biological activity of the enzyme glucose dehydrogenase.

The invention moreover relates to the plasmid pJH111 which contains the DNA sequence according to the invention coding for the glucose DH polypeptide.

The invention furthermore relates to a recombinant expression plasmid in which the entire coding region of the glucose DH gene is under the control of the $\lambda P_L$ promoter and determines the entire DNA sequence of the glucose DH gene. In place of the $\lambda P_L$ promoter, it is equally possible according to the invention to use as expression control sequence an *E. coli* promoter system such as the *E. coli* lac system, the *E. coli* lactamase system, the *E. coli* trp system or the *E. coli* lipoprotein promoter, a yeast expression control sequence or another eukaryotic expression control sequence. The only important points here are the functional linkage of the gene with the expression control sequence and the choice of a suitable expression control sequence for a particular host organism.

The invention particularly relates to the expression plasmid pJH115 which contains the DNA sequence according to the invention, which codes for the glucose DH polypeptide and includes the $\lambda P_L$ promoter.

The invention moreover relates to the polypeptide having the biological activity of glucose DH and the amino acid sequence which is indicated in FIG. 2 and can be synthesized on expression under the stated conditions. The invention also relates to the host organism containing the DNA according to the invention, in particular *E. coli* N100/pRK248/pJH115 into which the plasmid pJH115 has been transformed.

The invention moreover relates to mutants of the disclosed DNA sequences. The mutations can be produced by gene deletion, translocation, duplication or inversion by natural or technical, chemical, physical or biological methods. The mutations include point- and segment-mutations, preferably point mutations.

Finally, the invention relates to the use of the polypeptide according to the invention for the determination of glucose, in particular of blood glucose.

It is possible according to the invention, by use of the DNA sequence which encodes glucose DH and has been isolated from *Bacillus megaterium* as a probe molecule of genomic libraries of microorganisms producing glucose DH, to identify the corresponding gene and to isolate it from the genomic libraries. It is also possible in this way to prepare polypeptides having the biological activity of the enzyme glucose DH from other microorganisms, for example *Bacillus subtilis*, in any desired amount.

The species used to provide glucose DH are microorganisms of the species *Bacillus megaterium* and its mutants or variants which possess the appropriate genetic information. Strains of this species are known and deposited in authorized depositories, for example DSM 321, DSM 322, DSM 333 or DSM 337.

Suitable host organisms which can be transformed with DNA encoding glucose DH are primarily microorganisms, but can also be plant, animal or human cells. However microorganisms such as bacteria, yeasts and other fungi, in particular *E. coli* bacteria, are preferably used.

The process according to the invention is preferably carried out as follows.

Firstly, chromosomal DNA from *Bacillus megaterium* cells (for culturing, see Example 1) is isolated and purified using methods known from the literature (Example 4). The chromosomal DNA isolated from *Bacillus megaterium* is partially hydrolyzed in a manner known per se using restriction endonucleases which are customary and known to be suitable for this purpose and are, as a rule, commercially available. The restriction enzyme Sau3A is preferably used for this purpose. Hydrolysis is controlled in such a way that mainly fragments with a length between 9 and 22 kilobases (kb), preferably more than 14 kb, are obtained, because these are particularly suitable and advantageous for incorporation into the DNA of a phage vector. The aim is, for the cloning of the structural gene of glucose DH, to set up a genomic library of the appropriate Bacillus strain using a suitable phage vector. The known phage vector λ-EMBL3 (Frischauff et al., 1983, J. Mol. Biol. 170, 827–842) is preferably used for this purpose. The phage DNA is prepared as described in detail in Example 3 and is cut up in a known manner using customary restriction endonucleases, preferably BamHI. The size of the DNA fragments obtained in each case is determined by gel electrophoresis.

The DNA fragments from the Bacillus genome which fit into the cleavage site of the phage DNA are now incorporated using commercially available ligation enzymes, preferably $T_4$ DNA ligase, in a manner known per se (Example 5). The various recombinant phage molecules obtained in this way are transduced in a host organism which is able to multiply them, preferably *E. coli*, in particular *E. coli* NM539(Sup F hsd R lac Y $P_2COx3$) (ATCC 35 639) and cloned in a known manner (Arber et al. 1983, in "Lambda II", Cold Spring Harbor Monographs, 433-465). The transformation of E. coli strains is generally carried out by, for example, the calcium chloride method and is explained in detail in Example 6. The glucose DH gene is identified by detecting the enzyme activity in the lysate of the newly formed phage clones using a specific filter assay based on the glucose DH detection reaction described in the introduction. The formation of $NADH_2$, which accompanies the glucose DH production (positive reaction), is detected by the appearance of fluorescence signals from cells (plaques) which have been applied to filter paper and lysed by phages (Example 9). On the basis of these assays, which should be repeated where appropriate and are used in the subsequent working steps, it is possible finally to identify phage clones with a reproducibly positive reaction. To confirm the result, liquid lysate of the isolated clone is examined by spectrophotometry (334, 340 or 365 nm) and the substrate specificity is tested. This results in the data known from the literature being obtained (Pauly et al., 1975; Hoppe-Seyler's Z. Physiol. Chem. 356; 1613-1623).

In order to achieve concentration of the glucose DH DNA within the recombinant phage DNA, subcloning is carried out in a subsequent procedure, preferably in plasmids. For this purpose, the recombinant phage DNA is in turn partially hydrolyzed with restriction endonucleases, preferably Sau3A, as customary, so that fragments about 4-9 kb in size are produced. In principle, it is possible to use as starting plasmid any plasmid which is not destabilized on incorporation of DNA fragments of the size indicated. Particularly suitable for this purpose is the known plasmid pBR322 (origin: Bolivar et al., 1977, Gene 2, 95-113) which is preferably partially digested with the restriction endonuclease BamHI. The phage DNA fragments are now ligated in a manner known per se with the plasmid vector which has been cut open (Example 5). The ligation products are used to transform in a customary manner any desired host organism which is suitable for the transformation and is obtainable from a recognized depository, preferably E. coli (Example 6). The colonies obtained in this way are subjected to the glucose DH enzyme assay (Example 9). Several clones with a positive glucose DH reaction emerge from this. One of the plasmids thus obtained has a size of 10.2 kb and is called pJH 107. For the purpose of restriction analysis, the plasmid is completely hydrolyzed in a manner known per se by the restriction endonucleases EcoRI, SalI, SphI, HindIII and ClaI, and the DNA fragments are fractionated by agarose gel electrophoresis in a manner known per se. The size of the passenger fragment which contains the glucose DH sequence is found to be 5800 bp. FIG. 3 reproduces the restriction map of the plasmid pJH107 according to the invention.

The procedure for further localization of the gene on the recombinant plasmid is as follows, the manner of proceeding being described above and in the Examples or being general state of the art.

Digestion of pJH107 with restriction endonucleases which, with high probability, do not cut in the structural gene. SphI is preferably used for this purpose.

Figure 4:
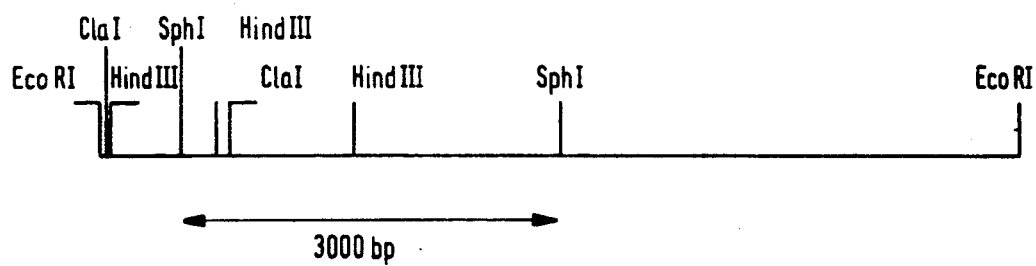

Incorporation of the thus obtained subfragments into the plastmid vector pBR322 and transformation and cloning of a host organism, preferably E. coli RR1. Recombinant plasmid vector according to the invention pJH 108 contains a passenger DNA fragment about 3000 bp in size (FIG. 4). The endonucleases SphI, ClaI, EcoRI and HindIII are preferably used in the restriction analysis.

Digestion of pJH108, preferably with HindIII.

Incorporation of the thus obtained subfragments into the plasmid vector pBR322 and transformation and cloning of a host, preferably E. coli. The recombinant plasmid vector pJH111 (DSM 4052P) of this invention is thus obtained (FIG. 5).

The plasmid vector pJH111 now contains, as restriction analysis shows, only a passenger DNA fragment 1100 bp in size in addition to the residual plasmid 5500 bp in size. The corresponding E. coli clones have glucose DH enzyme activity. Further reduction in size of the DNA fragment results in complete loss of enzyme activity. Hence the gene for glucose dehydrogenase is located on the 1100 bp fragment.

The nucleotide sequence of the glucose DH gene is determined, for example, by the method of Maxam and Gilbert (1980, Methods Enzymol., 65, 499-580). In this method, radiolabeled DNA is partially cleaved in four different base-specific reactions, the cleavage products are separated on a denaturing polyacrylamide gel and, after subsequent autoradiography, the sequence is established in a manner known per se (Example 7).

Figure 5:
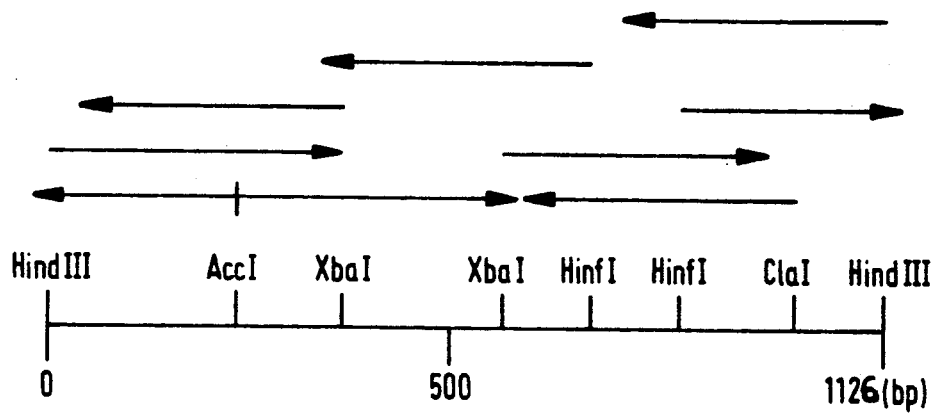

The sequencing strategy is depicted in FIG. 5. The new nucleotide sequence according to the invention which is to be assigned to the structural gene is reproduced in FIG. 1.

FIG. 2 shows the new amino acid sequence derived from the DNA sequence. It corresponds to that obtained by protein sequencing of the purified enzyme.

Expression of the polypeptide according to the invention, which is shown in FIG. 2, in a E. coli host with use of the plasmid vector pJH111 but without a specific E. coli promoter results, as indicated above, in enzyme activities of about 0.1 units/ml of culture on average. An expression vector is used in order to obtain a desired overproduction. An example of a suitable expression vector is pMR1 (origin: Rimmler, 1985, Dissertation, TH Darmstadt). This plasmid, which can be constructed from the plasmids pDS26t and pPlc28 known from the literature, contains the efficient $\lambda P_L$ promoter. The plasmid pPlc28, as well as the host bacterium E. coli W6 used for cloning, are disclosed in European Patent Application EP 00 41 767. In E. coli W6, the $\lambda P_L$ promoter is repressed by the chromosomally encoded cI repressor. pJH111 is cut with HindIII, and the 1100 bp fragment according to the invention is, after preparative gel electrophoresis on low melting agarose, isolated in a manner known per se. pMR1 is likewise preferably hydrolyzed with HindIII, and the cleavage products are ligated and transformed into E. coli W6 in a customary manner (Remaut et al., 1981, Gene 15, 81-93). The plasmid DNA is isolated as indicated (Example 3), and any desired E. coli strain which is suitable for transformation, which can be obtained from a recognized depository and into which the plasmid pRK248 (origin: Bernard et al. 1979, Gene 5, 59-76) has been cloned in a known manner is transformed. The latter carries the gene for the heatsensitive λ repressor and for tetracycline resistance. The newly constructed plasmid according to the invention is called pJH115 (DSM 4051P). Its construction is reproduced in FIG. 6. The host organism according to the invention is called E. coli N100/pRK248/pJH115. It is possible according to the invention to dispense with the presence of pRK248 if it is possible to use host organisms in which the λ repressor is chromosomally encoded (for example E.

*coli* W6). The host organism according to the invention exhibits the surprisingly high expressions indicated above and in FIG. 8. A typical expression experiment is described in Example 10.

Figure 10:
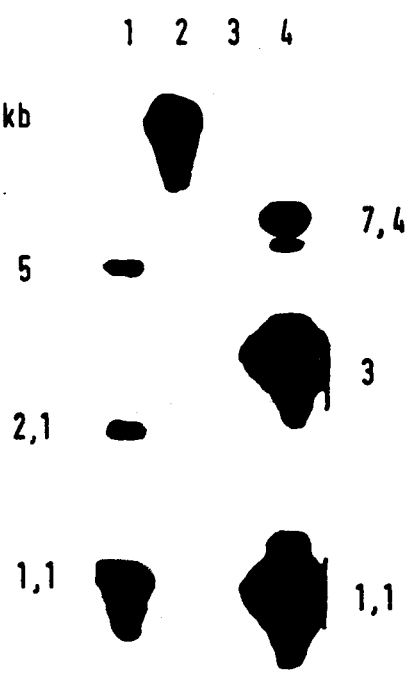

The differences between the amino acid sequence of the known glucose DH, and the amino acid sequence derived from the DNA according to the invention which codes for glucose DH, suggest that, besides the new enzyme according to the invention, there also exists a second enzyme or gene in *Bacillus megaterium*. The identification of isoenzymes of glucose DH is carried out by hybridization of filter-bound DNA from *Bacillus megaterium* with the radiolabeled 1127 bp HindIII fragment of the gene (Examples 7 and 8). For this purpose, in a manner known per se, chromosomal DNA is hydrolyzed with the restriction endonuclease HindIII, is applied together with DNA length standards to a 1% agarose gel and is transferred to nitrocelulose. The length standard used is not only SPP1 DNA hydrolyzed by Eco RI but also a mixture of pJH108 (SalI-SphI hydrolyzed) and pJH111 (HindIII hydrolyzed), which makes determination of the size of hybridized fragments possible after autoradiography. The hybridization technique and autoradiography are, where they are not explained in detail in the Examples, state of the art or can be deduced therefrom by the expert in a straightforward manner. It is possible to identify from the autoradiograph (FIG. 10) not only the intense 1100 bp band corresponding to the gene probe used but also weaker bands at 2100 and 5000 bp. This shows that *Bacillus megaterium* contains more than one glucose dehydrogenase gene.

Figure 11:
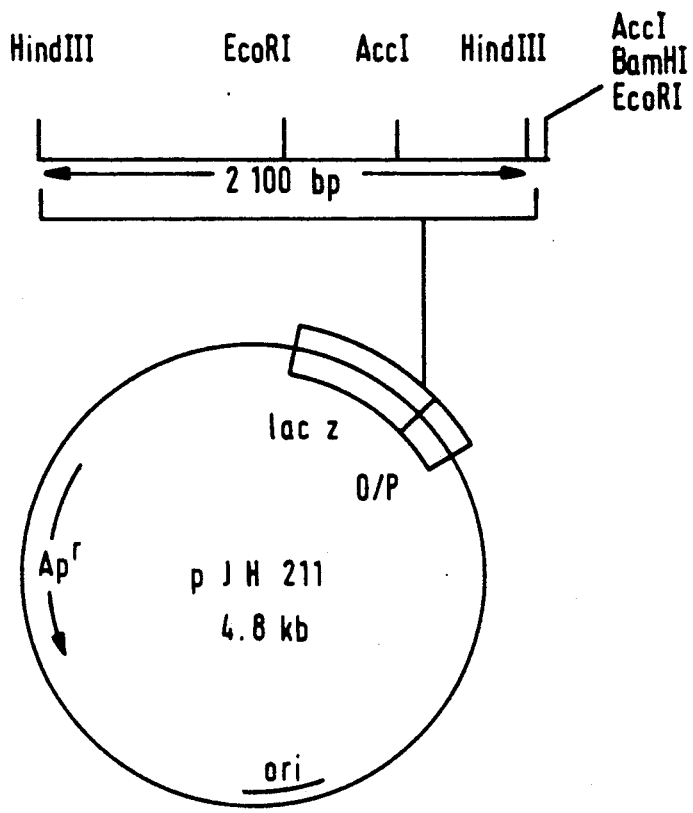

The cloning of another glucose DH corresponding to the fragments between 1300 and 5000 bp can, in principle, be carried out as described in detail above for the 1100 bp fragments. The vector used is the *E. coli* plasmid pUC18 (origin: Viera et al., 1982, Gene 19, 259). Finally obtained is the new plasmid pJH211 (FIG. 11) which contains a 2100 bp DNA fragment and which results in the expression in *E. coli* of glucose DH (the 5000 bp fragment which likewise hybridizes with the gene probe cannot be obtained in this way). The DNA and protein sequences of the second glucose DH gene are established in a manner known per se or in analogy to the 1100 bp fragment described above. The sequence corresponds entirely to that known for glucose DH. It is possible to construct in analogy to the *E. coli* strain *E coli* N100/pRK248/pJH115 according to the invention, which produces glucose DH, a corresponding overproduction strain for the second glucose DH: *E. coli* N100/pRK248/pJH215 provides, according to the invention, large amounts of high-quality glucose DH, the enzyme activity being about 20–30% lower than in the *E. coli* N100/pRK248/pJH115 system. The stability of the two isoenzymes is approximately comparable between 20° and 50° (preincubation).

The following abbreviations are used in the description and in the Examples and Figures in addition to those explained in detail there:

| A | Adenine |
|---|---|
| $A_{578}$ | Absorption at 578 nm |
| $A_{578}$-U | Unit of absorption at 578 nm |
| $Ap^R$ | Ampicillin resistance |
| APS | Ammonium peroxodisulfate |
| b | base |
| Bis | N,N,N',N'-methylenebisacrylamide |
| bp | Base pair |
| BSA | Bovine serum albumin |
| C | Cytosine |
| Ci | Curie (2.22 × $10^{12}$ disintegrations per min.) |
| cpm | Counts per minute |
| Da | Dalton (g/mol) |
| DNA | Deoxyribonucleic acid |
| DTT | Dithiothreitol |
| EDTA | Ethylenediaminetetraacetic acid |
| *E. coli* | *Escherichia coli* |
| G | Guanine |
| galk | Galactokinase |
| k | × $10^3$ |
| l | Liter |
| NAD | Nicotinamide-adenine dinucleotide |
| NADP | Nicotinamide-adenine dinucleotide phosphate |
| PEG | Polyethylene glycol |
| rpm | Revolutions per minute |
| s | Second |
| SDS | Sodium dodecyl sulphate |
| T | Thymine |
| T4 | Bacteriophage T4 |
| $Tc^R$ | Tetracycline resistance |
| TEMED | N,N,N',N'-tetramethylethylenediamine |
| Tris | Tris(hydroxymethyl)aminomethane |
| tRNA | Transfer ribonucleic acid |
| U | Unit of enzyme activity |

The Figures in which individual sections of the invention are depicted are explained below:

FIG. 1: DNA sequence of the glucose dehydrogenase gene(I) from *Bacillus megaterium*.

FIG. 2: Amino acid sequence of the expression product of pJH111 and pJH115.

FIG. 3: Restriction map of the plasmid vector pJH107.

The restriction cleavage sites which can be assigned unambiguously are indicated. The size of the passenger DNA is about 5800 bp. The plasmid pJH107 is constructed from the BamHI-digested plasmid pBR322 and the Sau3A-hydrolyzed construction of chromosomal DNA and λEMBL-3 phage DNA.

FIG. 4: Restriction map of the plasmid vector pJH108. Only the cleavage sites which can be assigned unambiguously are indicated. The size of the passenger DNA is about 3000 bp. The plasmid pJH108 is constructed from a fragment of pJH107 (SphI hydrolysed) and pBR332.

FIG. 5: Strategy for sequencing the 1127 bp fragment from pJH111. The arrows indicate the size of the identified sequence in each case. The plasmid pJH111 is constructed from the HindIII-digested fragment of pJH108 and pBR322.

Figure 6:
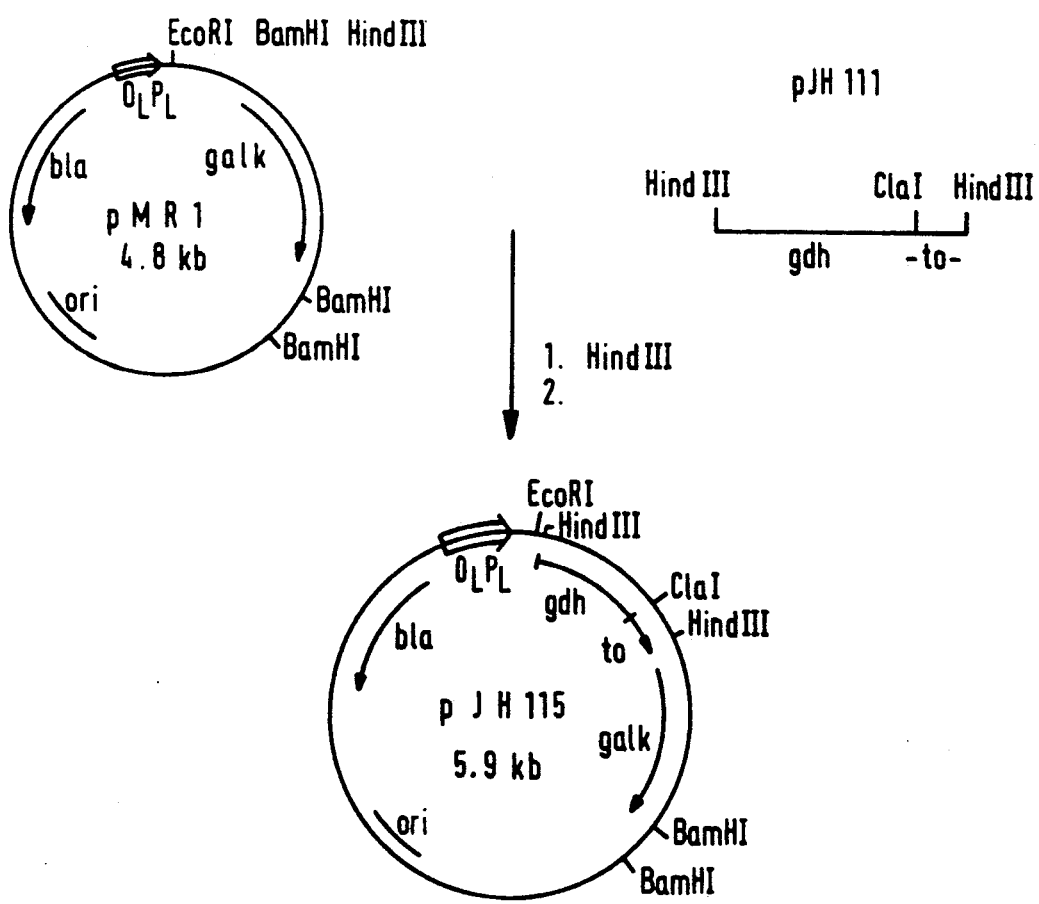

FIG. 6: Construction of the plasmid vector pJH115. This is constructed by HindIII hydrolysis of pMR1 and pJH111, followed by ligation.

bla: Beta-lactamase; gdh: glucose DH;
to: Terminator; galk: galactokinase;
$O_L P_L$: Promoter/operator region (λ $P_L$ promoter)
Ori: Replication origin FIG. 7: Protein sequence comparison between glucose DH, based on 1100 bp fragment (a) and glucose DH based on 2100 bp fragment (b; known sequence). The first 45 amino acids are depicted.

Figure 8:
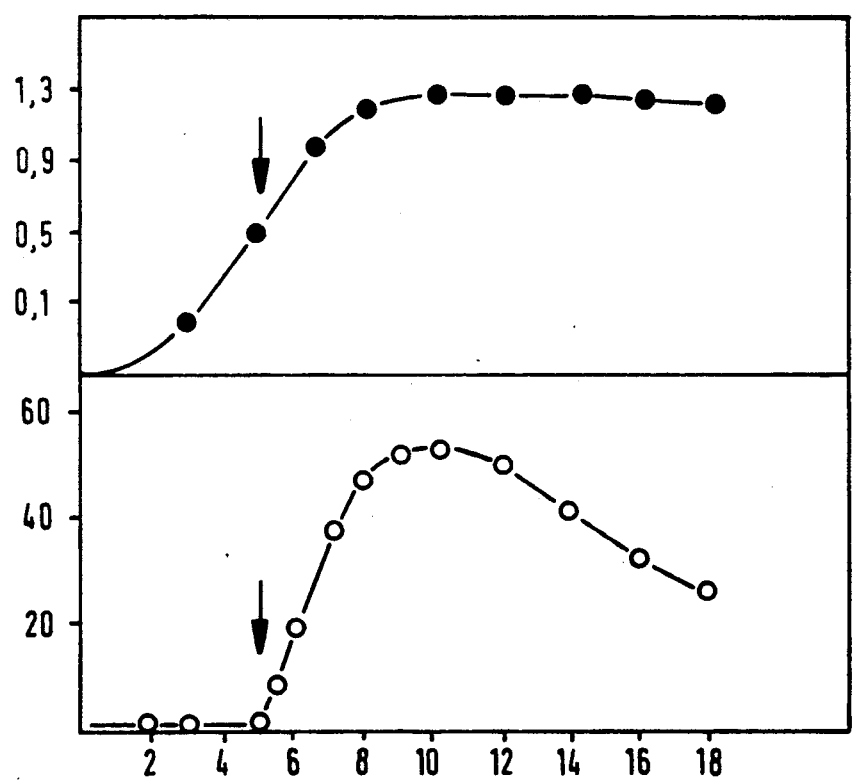

FIG. 8: Growth and expression curves (absorption at 578 nm and units/ml both as function of time (h) ) of *E. coli* N 100/pRK248/pJH115. Growth of bacteria in 20 mL of LB medium (Example 1) at 28°. At an optical density of 0.5 $A_{578}$-U the culture was transferred into a water bath at 42°, 1 $A_{578}$-U cell samples were removed and the enzyme activity was determined.

Figure 9:
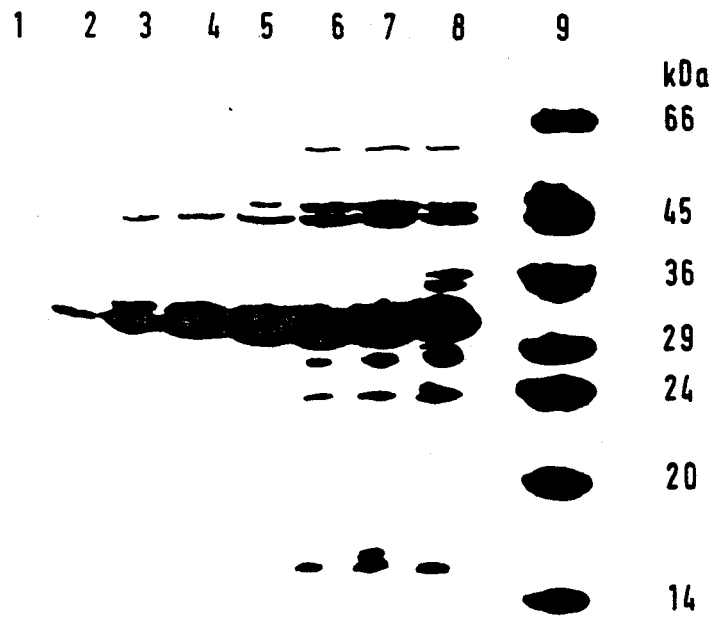

FIG. 9: Overproduction of glucose dehydrogenase in E. coli N100/pRK248/pJH115. Protein separation on a 12.5% SDS-polyacrylamide gel
  Track 1: Cell protein before induction
  Tracks 2–8: 0.5, 1–5 and 10 h after induction
  Track 9: Size standard FIG. 10: AUtoradiograph of the hybridization of chromosomal DNA from *Bacillus megaterium* with the radiolabelled 1100 bp DNA fragment from pJH111 or pJH115 after exposure for 12 h.
  Track 1: Chromosomal DNA (*Bacillus meg.*), HindIII hydrolyzed
  Track 2: Chromosomal DNA (*Bacillus meg.*), unhydrolyzed
  Track 3: SPP1 length standard
  Track 4: Mixture of 10 ng of each of:
    pJH108, SalI hydrolyzed,
    pJH108, SphI hydrolyzed
    pJH111, HindIII hydrolyzed FIG. 11: Restriction map of pJH211. Only the cleavage sites used for restriction analysis are indicated. The plasmid pJH211 is constructed from pUC18 and HindIII-hydrolyzed chromosomal DNA.

Figure 12:
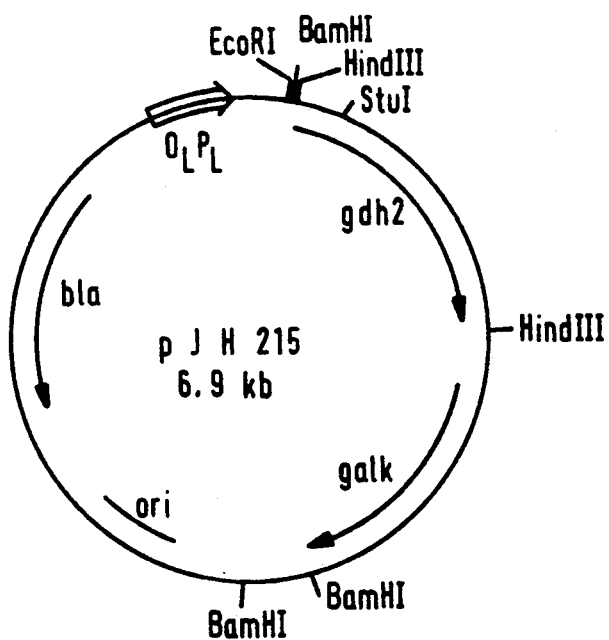

FIG. 12: Restriction map of pJH215. The plasmid pJH215 is constructed from pJH211 (HindIII hydrolyzed) and pMR1. Designations as in FIG. 6.

The Examples which follow are intended to explain the invention in detail. Throughout, the temperatures are given in degrees celsius.

EXAMPLE 1

Culturing of *E. coli* Bacteria a) For the preparation of plasmids in mg amounts, *E. coli* bacteria are cultured on the 1 l scale in complete (LB) or minimal (M9) medium. For this purpose, 1 l of medium is inoculated with 5 ml of a stationary preculture and cultivated, shaking continuously, at 37° for about 18 h until the stationary phase of growth has been reached.

b) For the overexpression of glucose dehydrogenase, 200 ml of LB medium is inoculated with 2 ml of an overnight culture grown at 28°. The suspension of bacteria is then cultivated at 28° and 160 r.p.m. until an optical density of 0.5 $A_{578}$-U is reached. The culture vessel is then incubated at 42° for a further 16 h.

a) LB Medium:

| | |
|---|---|
| Casein, enzymatically hydrolyzed | 10 g |
| Yeast extract | 5 g |
| NaCl | 5 g |
| Agar (solid agar) | 15 g |
| (soft agar) | 7.5 g |
| Double-distilled water ad | 1000 ml |
| pH adjusted to 7.4 with 1.0 N NaOH. | |
| Antibiotics were added in the following concentrations: | |
| Ampicillin: | 50 µg/ml |
| Tetracycline: | 20 µ/ml | b) Modified M9 medium:

| | |
|---|---|
| M9 salts, 10-fold concentrated | 10 ml |
| 20% glucose solution | 5 ml |
| 1 M MgSO$_4$ | 1 ml |
| 10% Casein hydrolyzate | 5 ml |
| Thiamine solution (2 mg/ml) | 0.1 ml |
| Double-distilled water ad | 1000 ml | c) M9 salts, 10-fold concentrated:

| | |
|---|---|
| Na$_2$HPO$_4$ × 2 H$_2$O | 75 g/l |
| KH$_2$PO$_4$ | 30 g/l |
| NH$_4$Cl | 10 g/l |
| NaCl | 5 g/l |

EXAMPLE 2

Preparation of λ Phages a) Plate Lysates

In order to prepare a relatively large number of recombinant phages from phage suspensions with a low titre, initially plate lysates are prepared.

For this purpose, $10^5$–$10^6$ phages in a volume of 100 µl are mixed with 100 µl of an overnight culture of the host strain *E. coli* NM 539 and incubated at 37°, without agitation, for adsorption of the phages. Then 3 ml of soft agar at 47°–50° are added, mixed in and the mixture is spread over a solid agar plate. After incubation at 37° for 16 hours, the soft agar layer is scraped off. The cell debris is then removed by centrifugation (10 min) at 10,000 r.p.m. and 4°. The supernatant is transferred into a sterile vessel, mixed with a few drops of chloroform and stored at 4°.

b) Liquid Lysate

Phages are obtained on a preparative scale by means of liquid lysates.

25 ml of LB liquid medium which contains 10 mM MgSO$_4$ and 0.4% maltose is inoculated with an overnight culture of the host strain *E. coli* NM 539. The suspension is incubated at 37°, with aeration, until about 1.3 $A_{578}$-U is reached. The bacteria are then infected with $10^6$ phages/ml and left at 37° C., without agitation, for 15 min for adsorption. Subsequently 1 l of LB medium at 37° is inoculated with the infected bacteria, and the mixture is incubated at this temperature, with aeration, until lysis occurs. The lytic event can be followed by spectrophotometry due to a rapid fall in the absorption at 578 nm. After the cell debris has been removed by centrifugation at 5000 r.p.m. and 4° for 15 min, the phages can be obtained in the aqueous supernatant.

EXAMPLE 3

Isolation of Vector DNA a) Isolation of Phage DNA

The suspension of phages purified by ultracentrifugation is adjusted to 20 mM EDTA, 0.5% SDS and, after addition of 50 µg/ml proteinase K, is incubated at 50° for 1 h. It is then extracted several times with the same volume of phenol and several times with chloroform/isoamyl alcohol (24:1). The DNA is precipitated in a known manner using ethanol, and is sedimented by centrifugation at 5,000 r.p.m. for 10 min. It is then washed with 70% ethanol, dried and taken up in buffer.

b) Minipreparation of Plasmids

In order to be able to analyze plasmids in a large number, the rapid lysis method of Birnboim (Birnboim and Doly, 1979: Nucl. acid Res. 7, 1513) is used.

1.5 ml samples of cell suspension from an overnight culture are sedimented by centrifugation at 15,000 r.p.m. for 1 min. After addition of 100 µl of solution A (see below) the mixture is incubated at 20° for 5 min. Then 200 µl of solution B (see below) are added, and the vessels are placed in ice. After a further 5 min, solution C (see below) is added, and the samples are left in ice until an insoluble complex of chromosomal DNA, RNA and protein precipitates (2-5 min). After one centrifugation (15 min) the plasmid-containing supernatants are transferred into new 1.5 ml plastic Eppendorf tubes.

The DNA is precipitated with ethanol at $-20°$ for 10 min and is sedimented in the centrifuge for 15 min. It is then washed twice with 70% ethanol and dried (in a desiccator).

After being taken up in 40 $\mu$l of TE buffer (see below) the DNA can be used directly for transformation or for restriction analyses:

| Birnboim solution A: | Birnboim solution B: |
|---|---|
| 25 mM Tris-HCl, pH 8.0 | 0.2 M NaOH |
| 50 m Glucose | .1% SDS |
| 10 mM EDTA | |
| Birnboim solution C: | TE buffer: |
| 3 M NaOAc/HOAc, pH 4.8 | 10 mM Tris base |
| | 1 mM HCl |
| | pH: 8.0 | c) Preparative Plasmid Isolation

Plasmids are prepared in mg amounts by means of a limited protoplast lysis by detergents (Hardies et al., 1979, J. Biol. Chem. 254, 5527-5534).

A suspension of bacteria from Example 1 is centrifuged at 5,000 r.p.m. at 4° for 20 min. The sediment is taken up in 15 ml of sucrose solution (25% sucrose in 50 mM Tris-HCL, pH 8.0). After addition of 3 ml of 0.5 EDTA and 3 ml of lysozyme solution (20 mg/ml lysozyme in 50 mM Tris-HCL, pH 8.0), the mixture is incubated in ice for 30-40 min. Then 2 ml of a 2:1 (v/v) mixture of 10% polyethylene glycol monolauryl ether/10% deoxycholate are added. The cell digest is clarified by centrifugation (30 min.) at 40,000 r.p.m. and 4°. The clear supernatant is decanted, 100 $\mu$g/ml of RNase A are added, and the mixture is incubated in ice for 45 min. To precipitate the DNA, the RNase-treated supernatant is mixed with half the volume of 30% PEG 6,000 in 1.5M NaCl and left in ice for a further 30 min. Centrifugation is at 8,000 r.p.m. at 4° for 20 min. The precipitate is taken up in 5 ml of TE buffer, and 50 $\mu$g/ml proteinase K are added, and the mixture is incubated at 37° for 60 min. It is then extracted several times with TE-saturated phenol and several times with chloroform/isoamyl alcohol (24:1). The DNA is precipitated with ethanol, washed and dried. The sediment is dissolved in 1-2 ml of TE buffer, and the plasmid yield is determined by spectrophotometry at 260 nm.

EXAMPLE 4

Preparation of Chromosomal DNA from *Bacillus megaterium* Cells Which Produce Glucose DH Bacterial cells from 100 ml of a stationary culture grown in complete medium are sedimented at 5,000 r.p.m. and 4° for 10 min. The sediment is then taken up in 10 ml of lysis buffer (50 mM NaCl, 50 mM EDTA, 30 mM Tris-HCl, pH 7.9); 40 mg of lysozyme are added, and the mixture is incubated at 37° for 45 min. The suspension is adjusted to 1% in SDS, 5 mg of proteinase K are added, and the mixture is left at 37° for a further 30 min. It is then extracted several times with TE-saturated phenol and several times with chloroform/isoamyl alcohol (24:1). The nucleic acids are precipitated, washed and dried in the customary manner.

To hydrolyze RNA which is still present, the sediment is cautiously resuspended in 5 ml of TE buffer, 10 $\mu$g/ml of RNase are added and the mixture is incubated at 37° for 30 min.

The solution is then adjusted to 1% SDS and 50 $\mu$g/ml in proteinase K and is treated at 37° for a further 30 min. It is then extracted with phenol and chloroform/isoamyl alcohol as described above and dialysed against TE buffer. The yield of chromosomal DNA from this method is between 2 and 4 mg.

EXAMPLE 5

Ligation of DNA

The formation of phosphodiester bonds between adjacent 3'-hydroxyl and 5'-phosphate groups is catalyzed by T4 DNA ligase.

The reaction is carried out in T4 DNA ligase buffer with a 5-fold excess of the DNA which is to be inserted over the vector DNA. The volume is 20 $\mu$l.

For DNA fragments with protruding single-stranded ends, the ligation is carried out at 4° with 1 U of enzyme per $\mu$g of DNA for 4-16 h. The ligation of double-stranded ends is carried out at 20° with 10 U of enzyme per $\mu$g of DNA for 4 h.

The reaction mixture is then used directly for the transformation (Example 6).

| T4 DNA Ligase buffer: | 0.4 mM | ATP |
|---|---|---|
| | 66 mM | Tris-HCl, pH 7.6 |
| | 6.6 mM | $MgCl_2$ |
| | 10 mM | DTT |

EXAMPLE 6

Transformation of *E. coli* (Calcium Chloride Method)

a) Preparation of Competent *E. coli* Cells

*E. coli* cells are cultivated in 20 ml of LB medium untill an optical density of about 0.5 $A_{578}$-U is reached. The suspension is transferred into a precooled centrifuge tube and then placed in ice for 10 min. The bacteria are sedimented at 8,000 r.p.m. at 4° for 10 min. The supernatant is decanted and then the cells are washed with 20 ml of ice-cold 0.1M $MgCl_2$ solution and centrifuged as described. They are then taken up in 1 ml of ice-cold 0.1 m $CaCl_2$ solution and left in ice for at least 2 h.

b) Transformation of Competent *E. coli* Cells

For the transformation, 200 $\mu$l of competent cells are mixed with 50 ng of plasmid DNA and placed in ice for 30 min. The mixture is then heated in a water bath (42°) for 2 min. (heat pulse). After addition of 1 ml of LB medium, the mixture is incubated at 37° for 1 h (recovery phase).

200 $\mu$l samples of this suspension of bacteria are then plated out on selective nutrient media. The plates are incubated at 37° C. for 16-24 h.

For the transformation of the heat-sensitive *E. coli* strain N 100 pRK 248 cIts, all the incubation steps are carried out at 28°. The heat pulse is effective at 34° for 5 min.

EXAMPLE 7

Radiolabeling of DNA

Radiolabeled DNA fragments with a specific activity $>10^8$ cpm/$\mu$g are prepared using *E. coli* DNA polymerase I by repair synthesis (nick translation) in the presence of $\alpha^{32}$p-deoxynucleotides.

Mixture:

| | |
|---|---|
| 0.2 µg of DNA | |
| 2 µl of 10 × DNA polymerase buffer | |
| 1 µl each of 1.2 mM dNTPs (nucleotides 1-3) | |
| 5 µl of $\alpha^{32}$P-dNTP (3,000 Ci/mmol, | |
| 10 µCi/µl) (nucleotide 4) | |
| 0.5 µl of DNase I (60 pg/µl) | |
| Leave to react at 20° for 1 min, and add | |
| 10 U of DNA polymerase I | |

10×DNA polymerase buffer:

| | |
|---|---|
| 500 mM Tris-HCl, pH 7.8 | |
| 50 mM MgCl$_2$ | |
| 100 mM β-Mercaptoethanol | |
| 0.05% BSA | |

The reaction is carried out after addition of DNA polymerase I at 14° for 2-4 h and is stopped with 20 µl of 60 mM EDTA, pH 8.0. The volume is then increased to 100 µl with H$_2$O.

To remove unreacted nucleotides, the samples are mixed with 100 µl of 5M ammonium acetate solution and 400 µl of absolute ethanol and frozen in liquid nitrogen for 2 min. The radiolabeled DNA fragments are then sedimented in a bench centrifuge for 15 min., washed with 70% ethanol and dried. Unreacted nucleotides remain in the supernatant.

The DNA is taken up in 100 µl of H$_2$O and subsequently used for hybridization experiments.

EXAMPLE 8

Hybridization of Filter-Bound DNA

The hybridization of filter-bound DNA is carried out in solutions containing 50% formamide. To block non-specific binding sites, the nitrocellulose filters coated with DNA fragments are sealed, together with the prehybridization solution covering them, in plastic film, without air bubbles, and incubated at 42° for 3 h.

Prehybridization solution:

| | |
|---|---|
| 50% | formamide |
| 5x | concentrated Denhardt's solution |
| 5x | concentrated SSC (see below) |
| 0.5% | SDS |
| 100 µg/ml | tRNA from yeast |

Denhardt's solution:
0.02% BSA
0.02% Polyvinylpyrrolidone
0.02% Ficoll (polysucrose)
SSC:
150 mM NaCl
15 mM Sodium citrate, pH 7.2

For the hybridization, first the radiolabeled, double-stranded DNA probe is denatured by heating at 80° for 10 minutes and is then immediately cooled in ice.

The nucleic acids, which are now in the form of single strands, are then transferred into 20-30 ml of hybridization solution. This is used to replace the prehybridization solution, and incubation at 42° is carried out for a further 20 h.

Hybridization solution:

| | |
|---|---|
| 50% | formamide |
| 5x | concentrated Denhardt's solution |
| 5x | concentrated SSC |
| 0.5% | SDS |
| 10 mM | EDTA |
| 100 µg/ml | tRNA from yeast |
| 10$^6$ cpm/ml | radiolabelled DNA |

To remove non-specifically bound DNA, after the hybridization the filters are washed first several times with 200 ml of 2×concentrated SSC, 0.1% SDS at 20° and then several times with 10% SSC, 0.1% SDS at 42°.

EXAMPLE 9

Enzyme Assay for Glucose DH

For this assay, non-fluorescent chromatography paper is sprayed evenly with 92 ml of indicator solution and then dried at 20°.

Indicator solution:
60.5 ml of sodium phosphate buffer (0.12M; pH 7.6)
30 ml of D-glucose solution (10% w/v)
1.5 ml of NAD$^+$ solution (70 mg/ml)

Before the enzyme assay is carried out, the prepared chromatography paper is cut to the correct size of the nutrient media plates (diameter about 8 cm).

To carry out the assay for phage lysates, the plates are removed from the incubator immediately after the formation of readily visible plaques (600-800 per plate). The Petri dishes are first labeled and identically marked assay filters are placed on to cover exactly. After 2 min., they are removed, dried in a stream of hot air and then inspected under light of wavelength 366 nm. If active glucose DH has been transferred to the assay filters then NAD$^+$ can be reduced to NADH at these points and can be distinctly detected by fluorescence. Then, with the aid of the filter labelings, positive phage clones on the nutrient media plate are identified and isolated.

To carry out the assay for bacterial clones, cells are transferred in an identical manner to two nutrient media plates (100-200 colonies per plate). While one of the plates serves as reference plate ("master plate"), the other is used for the enzyme assay. This entails the bacteria being transferred to aluminium foil, and about 5 µl of the digestion solution being pipetted onto each colony. For the lysis, the cells are incubated at 20° in a moisture chamber for 30 min. Then, as described above, a test filter is placed on and dried, and the site of the enzymatic reaction is identified. The corresponding positive bacteria on the reference plate can then be used for plasmid isolation (Example 3).

Digestion solution:

| | |
|---|---|
| 100 mM | Sodium phosphate buffer, pH 6.5 |
| 20 mM | EDTA |
| 5 mg/ml | Lysozyme |

The activity is determined in a spectrophotometer at 25°.

Assay solution:

| | |
|---|---|
| 120 mM | Sodium phosphate buffer, pH 7.6 |
| 100 mM | Glucose |
| 2 mM | NAD$^+$ |

The enzyme activity (U/ml) is reported in μMol of substrate converted per min.

EXAMPLE 10

Preparation of the Glucose DH Expressed in *E. coli* N 100/pRK 248/pJH 115

A 10 l laboratory fermenter is charged with 7.5 l of LB medium, and is sterilized and then inoculated with 200 ml of a stationary culture of the overproduction strain. The cells are cultured at 28° with aeration. After an optical density of about 0.5 $A_{578}$-U is reached, the temperature is raised to 42°, and the culture is incubated with aeration for a further 5 h.

To prepare the glucose DH, the bacteria (about 10 g wet weight) are sedimented and then disrupted by grinding in a mortar with the same amount of alumina at 4°. After addition of 12.5 ml of $P_{50}$ buffer (50 mM potassium phosphate, pH 6.5; 0.1 mM 2-mercaptoethanol; 2 μg of phenylmethylsulfonyl fluoride) and 50 μg of DNase I, the mixture is incubated at 4° for 1 h. The alumina is removed by centrifugation at 8,000 r.p.m. and 4°. The aqueous supernatant is then clarified by centrifugation at 15,000, r.p.m. and 4° for 30 min.

The cell disruption solution is then mixed with 100 ml of $P_{50}$ buffer and absorbed onto a DE-52 column. After washing with 100 ml of $P_{50}$ buffer, proteins are eluted using a linear gradient from 0.05 to 0.5M KCl in $P_{50}$ buffer, and collected in 5 ml fractions. The elution volume is 1 l. To construct an elution profile, the absorption at 280 nm and the glucose DH activity in the individual fractions are determined.

The results of the protein purification are compiled in the table which follows.

| Purification stage | Purification of glucose DH | | |
| --- | --- | --- | --- |
| | Total activity (U) | Total protein (mg) | Specific activity (U/mg) |
| Bacterial disruption | 52,800 | 1 130 | 46.7 |
| Ammonium sulphate precipitation | 49,500 | 1 000 | 49.5 |
| DE-52 column (fractions 58-68) | 6,880 | 29.4 | 234 |

To check the homogeneity of the enzyme, samples are analyzed on a 12.5% SDS polyacrylamide gel.

Each of the plasmids and microorganisms disclosed herein by way of a DSM number has been deposited with the German Collection of Microorganisms, Grisebachstraase 8, D-3400 Göttingen, Germany.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A DNA molecule consisting essentially of the sequence (I), or a degenerate equivalent thereof,

ATG—TAT—ACA—GAT—TTA—AAA—GAT— (I)

—AAA—GTA—GTT—GTA—ATT—

ACA—GGT—GGA—TCA—ACA—GGT—TTA—

—GGA—CGC—GGA—ATG—GCT—

GTT—CGT—TTC—GGT—CAA—GAA—GAA—

—GCA—AAA—GTT—GTT—ATT—

AAC—TAT—TAC—AAC—AAT—GAA—GAA—

—GAA—GCT—CTA—GAT—GCG—

AAA—AAA—GAA—GTA—GAA—GAA—GCA—

—GGC—GGA—CAA—GCA—ATC—

ATC—GTT—CAA—GGC—GAT—GTA—ACA—

—AAA—GAA—GAA—GAC—GTT—

GTA—AAT—CTT—GTT—CAA—ACA—GCT—

—ATT—AAA—GAA—TTT—GGT—

ACA—TTA—GAC—GTA—ATG—ATT—AAC—

—AAC—GCT—GGT—GTT—GAA—

AAC—CCA—GTT—CCT—TCT—CAT—GAG—

—CTA—TCT—CTA—GAT—AAC—

TGG—AAC—AAA—GTT—ATT—GAT—ACA—

—AAC—TTA—ACA—GGT—GCA—

TTC—TTA—GGA—AGC—CGT—GAA—GCA—

—ATT—AAA—TAC—TTC—GTT—

GAA—AAC—GAC—ATT—AAA—GGA—AAT—

—GTT—ATC—AAC—ATG—TCT—

AGC—GTT—CAC—GAA—ATG—ATT—CCT—

—TGG—CCA—TTA—TTT—GTT—

CAC—TAC—GCA—GCA—AGT—AAA—GGC—

—GGT—ATG—AAA—CTA—ATG—

ACG—GAA—ACA—TTG—GCT—CTT—GAA—

—TAT—GCG—CCA—AAA—GGT—

ATT—CGC—GTA—AAT—AAT—ATT—GGA—

—CCA—GGT—GCG—ATG—AAC—

ACA—CCA—ATT—AAC—GCA—GAG—AAA—

—TTT—GCA—GAT—CCA—GAA—

CAA—CGT—GCA—GAC—GTA—GAA—AGC—

—ATG—ATT—CCA—ATG—GGT—

TAC—ATC—GGT—AAA—CCA—GAA—GAA—

—GTA—GCA—GCA—GTT—GCA—

GCA—TTC—TTA—GCT—TCA—TCA—CAA—

—GCA—AGC—TAT—GTA—ACA—

GGT—ATT—ACA—TTA—TTT—GCA—GAT—

—GGC—GGT—ATG—ACG—AAA—

-continued
TAC—CCT—TCT—TTC—CAA—GCA—GGA—

—AGA—GGC—TAA—TAG wherein the reading frame starts at the first nucleotide, wherein the polypeptide coded for by the DNA molecule has the biological activity of the enzyme glucose dehydrogenase.

2. A DNA sequence of claim 1 which originates from *Bacillus megaterium*.

3. A recombinant cloning vector comprising a DNA sequence of claim 2.

4. A microorganism or cell culture transformed with a vector of claim 3.

5. A transformed microorganism of claim 4 which is *E. coli*.

6. *E. coli* N100/pRK248/pJH115 (DSM 4047), a microorganism of claim 5.

7. A method for producing a polypeptide having the biological activity of the enzyme glucose dehydrogenase comprising expressing the DNA encoding said polypeptide of a vector of claim 3 in a host cell grown under conditions wherein the polypeptide is expressed.

8. A recombinant cloning vector comprising a DNA sequence of claim 1.

9. A microorganism or cell culture transformed with a vector of claim 8.

10. A method for producing a polypeptide having the biological activity of the enzyme glucose dehydrogenase comprising expressing the DNA encoding said polypeptide of a vector of claim 8 in a host cell grown under conditions wherein the polypeptide is expressed.

11. A recombinant cloning vector of claim 8, wherein said sequence is functionally connected to an expression control sequence.

12. A recombinant cloning vector of claim 11, wherein the control sequence is a promoter which is capable of expressing said DNA sequence in *E. Coli* and/or *Bacillus megaterium*.

13. Plasmid pJH111 (DSM 4052P), a plasmid of claim 12, comprising a *Bacillus megaterium* promoter system.

14. A method for producing a polypeptide having the biological activity of the enzyme glucose dehydrogenase comprising expressing the DNA encoding said polypeptide of a vector of claim 13 in a host cell grown under conditions wherein the polypeptide is expressed.

15. Plasmid pJH115 (DSM 4051P), a plasmid of claim 12, comprising an *E. coli* promoter.

16. A method for producing a polypeptide having the biological activity of the enzyme glucose dehydrogenase comprising expressing the DNA encoding said polypeptide of a vector of claim 15 in a host cell grown under conditions wherein the polypeptide is expressed.

17. A DNA sequence of claim 1, consisting essentially of the sequence (I).

* * * * *